(12) United States Patent
Petersen

(10) Patent No.: US 7,601,155 B2
(45) Date of Patent: Oct. 13, 2009

(54) INSTRUMENTS AND METHOD FOR MINIMALLY INVASIVE SURGERY FOR TOTAL HIPS

(76) Inventor: Thomas D. Petersen, 9680 Alto Dr., La Mesa, CA (US) 91941

( * ) Notice: Subject to any disclaimer, the term of this patent is extended or adjusted under 35 U.S.C. 154(b) by 276 days.

(21) Appl. No.: 10/441,182

(22) Filed: May 20, 2003

(65) Prior Publication Data

US 2004/0236341 A1  Nov. 25, 2004

(51) Int. Cl.
*A61B 17/90* (2006.01)
*A61B 17/16* (2006.01)
*A61B 17/15* (2006.01)

(52) U.S. Cl. .................................... 606/89; 606/85
(58) Field of Classification Search ............ 606/79–80, 606/62, 86–89, 84, 85, 67; 623/22.12
See application file for complete search history.

(56) References Cited

U.S. PATENT DOCUMENTS

| 5,601,564 A * | 2/1997 | Gustilo et al. ............ 606/86 R |
| 6,494,913 B1 * | 12/2002 | Huebner .................. 623/19.11 |
| 6,780,190 B2 * | 8/2004 | Maroney .................... 606/86 |
| 2003/0050643 A1 * | 3/2003 | Taft .............................. 606/86 |
| 2003/0114859 A1 * | 6/2003 | Grusin et al. ................ 606/87 |

FOREIGN PATENT DOCUMENTS

| DE | 43 24 134 C1 * | 1/1995 |
| DE | 298 19 754 U1 * | 3/1999 |
| RU | 2 089 112 C1 * | 9/1997 |
| SU | 1210802 A * | 2/1986 |

* cited by examiner

*Primary Examiner*—David H. Willse
(74) *Attorney, Agent, or Firm*—H. Jay Spiegel

(57) ABSTRACT

An intramedullary femoral broach aligns two instruments. A femoral neck resector guide slides over the broach and centers on the patient's femoral head to determine the height and angular rotation of resection. A circular ring of the head and cutting arms assure the system will fit any femur. A template is applied to the femoral broach and seats itself against the buttress of the broach locking it into place. The broach is then reinserted into the intramedullary canal. When the template reaches the greater trochanter the sizer is adjusted to the rotational anteversion of the canal. The handle of the femoral broach is struck with a mallet until the template is imbedded into the proximal femoral neck intramedullary bone. A retractor facilitates reaming of the acetabulum through a small anterior incision. A proximal portion digs into the bone of the superior acetabulum to allow for retraction of soft tissues.

22 Claims, 7 Drawing Sheets

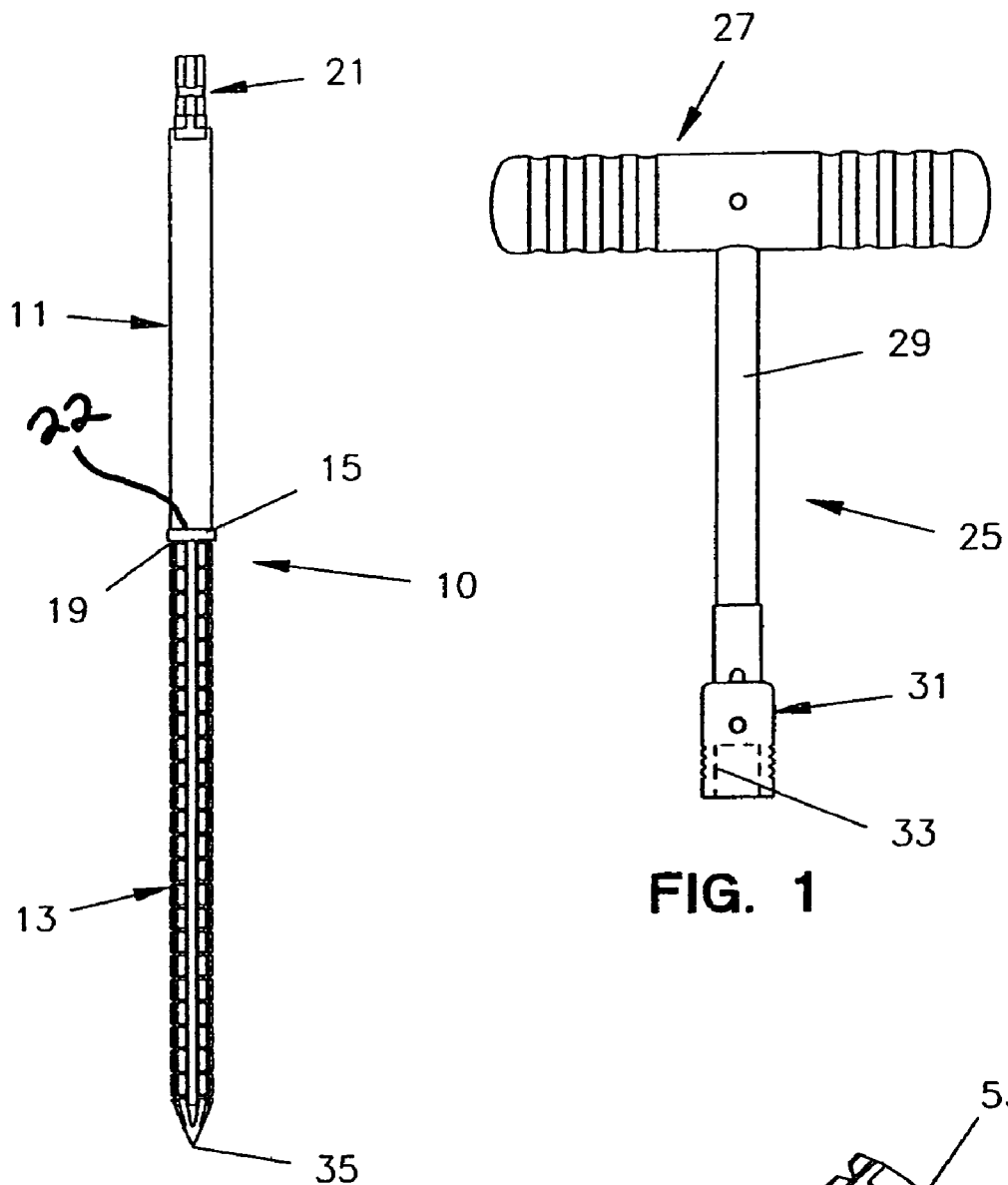
FIG. 1
FIG. 2
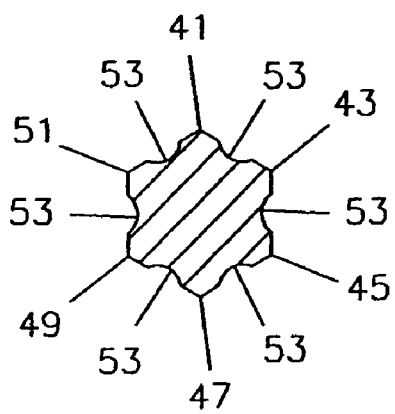
FIG. 3B
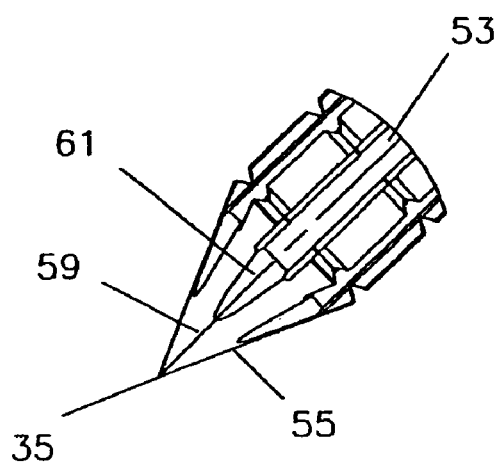
FIG. 3A

INSTRUMENTS AND METHOD FOR MINIMALLY INVASIVE SURGERY FOR TOTAL HIPS

BACKGROUND OF THE INVENTION

Minimally Invasive Total Hip Surgery denotes a surgical procedure that has been engineered to minimize the extent of the incision and separation of normal tissues. Its advantages include: less pain, less blood loss and faster recovery time with earlier release from the hospital. Its disadvantages include poor visibility, lost of normal landmarks and technical difficulties due to lack of exposure. These disadvantages can be countered with improved instruments and retractors. This invention describes one such system.

To appreciate the mechanical problems that the surgeon faces with Total Hip surgery, one needs to understand the advantages and disadvantages of the various surgical approaches to the hip joint.

Choice of incision is usually based on the surgeon=s training and experience. The Posterior/Posterior-Lateral incisions are superior for preparation of the femur, but decidedly hamper the correct attitude of the acetabulum reaming, which has to be a straight 40 degrees abduction and 20 degrees of adduction which favors the Anterior incision. In the Posterior incision, the femur is dislocated anterior to the acetabulum and interferes with the correct attitude of the reamer. Without releasing the Gluteus Maximus the femur cannot dislocate far enough to allow the reamer to be in the correct plane. This involves considerable soft tissue release to do the job properly.

The Anterior incision is great for acetabular reaming but difficult for preparation of the proximal femur, which has to be hyper-extended. To do so, the knee is dropped off the edge of the operative table and externally rotated to expose the femoral head and neck. In heavy people, this can be a major challenge for the surgeon. Also, the femur must be dislocated anteriorly during the reaming process because all the posterior structures are intact.

The optimal choice would be to combine both incisions to take advantage of the exposure that both offer. The Posterior incision is made first, therefore the femur can be dislocated Posteriorly for acetabular reaming using the Anterior incision. Normally, with a single anterior incision, the femur is dislocated anteriorly because of the intact posterior capsule. By using both incisions, the capsular releases are complimentary and allow for much less soft tissue release and exposure, hence the present invention uses two 3-inch incisions with excellent visibility of the task at hand.

If small incisions are to work, then the operation will have to be highly engineered with supportive instruments to the relatively blind, trusting surgeon. These instruments must facilitate the various tasks without full exposure.

The most difficult mechanical problems faced by orthopedists during the Total Hip operation are: 1) Accurate resection of the femoral neck; 2) Axial placement of the femoral stem into the intermedullary canal; 3) Accurate sizing of the femoral prosthesis; 4) Adequate visibility of the acetabulum; and 5) Proper attitude of the acetabular reamer.

1) Accurate resection of the femoral neck.

The minimal incision makes it difficult to evaluate leg length and level of femoral neck resection because only the femoral head and neck are extended from the incision. This negates all the known template guides for femoral neck resection and femoral head height. Without the template guides, a preliminary femoral neck resection would have to be made guessing at the correct plane for the femoral ante-version. This "approximate cut" can cause subsequent problems.

2) Axial placement of the femoral stem into the intermedullary canal.

A perpetual problem for orthopedists is inserting the femoral stem parallel to the intermedullary canal. This problem is aggravated by the fact that most prosthetic systems have an "abductor lever arm" less than the actual lever arm present so physicians tend to match the present lever arm (femoral neck angle) by tilting the prosthesis into "varus", a down-ward tilt. This attitude of the femoral prosthesis can lead to lateral thigh pain and early loosening of the prosthesis.

3) Accurate sizing of the femoral prosthesis.

Traditionally, sizing of the femoral prosthesis is done by progressive broaching of the femoral canal and is usually based on the maximum size of the femoral canal down near the tip of the stem. This system of instruments is based primarily on an optimum press-fit of the proximal femur that provides optimal stability and insures proximal loading of the prosthesis minimizing stress shielding and subsequent atrophy of bone.

4) Adequate visibility of the acetabulum and 5) proper attitude of the acetabular reamer.

If small incisions are to be employed, visibility and attitude issues must be addressed.

With these mechanical problems in mind the present invention was developed. There are four unique instruments in this invention that act in concert, which are the basis of this patent application.

SUMMARY OF THE INVENTION

The present invention relates to four unique instruments that facilitate a method of Minimally Invasive Total Hip surgery. The preferred method of use is disclosed, but individual surgeons may elect to use the instruments in their preferred techniques and exposures. The two exposures to the hip joint, as described, are not unique nor is the concept of two incisions unique for minimally invasive Total Hip surgery. The surgical procedure is explained to highlight the unique instruments and the mechanical problems they solve. Since this is an instrument system and method, and the unique instruments act in concert, they are disclosed together.

The instruments used in practicing the present invention are the following:

1) Intermedullary Femoral Broach which is unique because of several features, as follows:
   a) The tip is multi-sided and angled at 30 degrees with multiple cutting flanges that allow the tip to manually cut bone.
   b) The distal region has similar cutting flanges that facilitate manual reaming of the intermedullary canal.
   c) There is a mechanical buttress or shoulder at the junction of the cutting portion of the broach and the more proximal circular portion that locks the Cutter/Template in place when sizing the proximal femur.

This broach solves several problems: (1) it facilitates precise reaming into the intermedullary canal manually especially side cutting of the greater trochanter; (2) it provides a central axis for the Femoral Neck Resector Guide; and (3) it provides a central axis guide for the Sizer/Template.

2) The Femoral Neck Resector Guide is unique due to several features:
   a. It keys off the axially placed Intermedullary Femoral Broach guaranteeing accurate axially based cuts for the femoral neck.

b. The height and angle of resection is based on an adjustable ring that sits on top of the femoral head and also determines the correct amount of anteversion (rotation) of the resection from this adjustable ring.

c. Two captured cutting arms, one for the right hip and one for the left hip, have slide adjustments that allow them to fit snugly against bone regardless of the size of the femur.

d. The cutting head is contoured adjacent to the femoral neck for a snug fit. This Femoral Neck Resection Guide solves the following problems: (1) determining, with accuracy and precision, the height of the femoral neck cut; (2) determining, with accuracy and precision, the rotation of the normal anteversion of the patient; (3) ensuring that the resection is axially based on the central axis of the femoral canal; and (4) ensuring that the resection is accurate due to the captured saw guide that prevents tilting of the saw blade.

3) The Sizer/Cutter Template is unique in light of several features:

a) It keys off the Intermedullary Femoral Broach, which guarantees that there is adequate resection laterally, which is a perpetual problem. It actually makes a precise cut in the greater trochanter the exact size of the prosthesis as well as of the residual femoral neck.

b) The underside of the Template has a cutting edge much like a "cookie cutter" that clearly demarks the bone to be removed, thereby facilitating a precise fit.

c) The Template can easily be adjusted to the precise angulation of the femoral anteversion of the patient.

d) Since the Template is locked onto the Intermedullary Broach under the buttress, it can be easily held in the correct attitude and pounded into the bone by striking the handle of the broach.

The Sizer/Cutter Template solves the following problems: (1) ensuring that the prosthesis is axially aligned; (2) determining the optimal size of the prosthesis for the patient; (3) facilitating ante-version alignment; and (4) providing a precise fit for the prosthesis in the proximal femur.

4) The Anterior Acetabulum Retractor is unique because of several features:

a) It is essentially a right-angled retractor curved backwards that allows the surgeon to push it upward to retract the overlying tissues.

b) The proximal end has a curved portion with angulated teeth that are designed to fit onto the superior acetabulum and acts as a fulcrum for elevating the tissues away from the acetabulum.

c) The desired angle of retraction is roughly 45 degrees to minimize tissue disruption, so the proximal arm is relatively long compared to standard retractors.

The Anterior Acetabulum Retractor solves the following problems: (1) Since the 3 inch skin incision is relatively distal to the hip, retraction of the tissues upward over a length of 5 inches requires a specially designed retractor that is pried upward rather than downward as most retractors; and (2) the broad-based curved end with angulated teeth digs into the superior edge of the acetabulum providing a secure fulcrum for the retractor.

Advantages of the present invention include the following:

A) The strength of the present invention is the instrumentation provided to make an accurate resection of the femoral neck. This resection needs to be accurate in 3 planes or degrees of freedom. The instruments are based on the prosthetic design that will replace the resected femoral head and neck. This resection level needs to be identified from a reliable boney landmark that maintains the patient's leg length and the proper attitude that matches the inclination of the prosthesis and the anteversion (rotation) of the femoral head and needs to be axially based from the center of the intermedullary canal. Furthermore, it needs a captured saw guide to ensure the resection is accurate. The present invention addresses these difficult problems.

B) The present invention uses an axial hand reamer that enters the intermedullary canal in a specific location that provides that the reamer is positioned in the proper location laterally. The subsequent resections on the femoral neck and proximal sizing of the maximum femoral stem are keyed to this axially placed rod that prevents "varus" inclinations of the prosthesis.

C) The present invention uses a series of "cookie cutter" templates that match the femoral sizes proximally and are keyed off of the centrally placed axial rod. This ensures that adequate bone is removed laterally for proper placement of the femoral stem. Also placing the template in the proper degree of anteversion is very easy with the inventive system. A single slightly undersized broach is then used to compress the remaining cancellous bone for the optimal press-fit.

D) Adequate visibility of the acetabulum and proper attitude of the acetabular reamer are accomplished through a separated 3 inch incision anteriorly. This is basically a muscle sparing technique that only requires opening the hip capsule anteriorly with special retractors that allow good exposure to the acetabulum and the proper reaming attitude, which is about 40 degrees.

These four instruments acting in concert greatly facilitate the minimally invasive Total Hip operation.

As such, it is a first object of the present invention to provide instruments and method for minimally invasive surgery for Total Hips.

It is a further object of the present invention to provide instruments designed to be used together to facilitate total hip surgery that is minimally invasive.

It is a further object of the present invention to provide such a system in which an intramedullary femoral broach is installed and other instruments are aligned by keying off physical structures of the intramedullary femoral broach.

It is a still further object of the present invention to provide a femoral neck resection guide that keys off the intramedullary femoral broach and guarantees accurate cuts of the femoral neck in three planes or degrees of freedom.

It is a still further object of the present invention to provide a template that sizes and cuts while keying off the intramedullary femoral broach to increase precision in the resection of the greater trochanter.

It is a still further object of the present invention to provide an anterior acetabulum retractor that is curved backwards to facilitate the surgeon pushing it upward to retract overlying tissues.

These and other objects, aspects and features of the present invention will be better understood from the following detailed description of the preferred embodiment when read in conjunction with the appended drawing figures.

BRIEF DESCRIPTION OF THE DRAWINGS

FIG. 1 shows a front view of the Intramedullary Femoral Broach handle.

FIG. 2 shows a front view of the Intramedullary Femoral Broach.

FIG. 3a shows a perspective view of the Femoral Broach cutting tip.

FIG. 3b shows an end view of the Femoral Broach cutting tip.

FIG. 4b shows a cross-sectional view along the line 4b-4b of FIG. 4a.

SPECIFIC DESCRIPTION OF THE PREFERRED EMBODIMENT

Figure 4A:
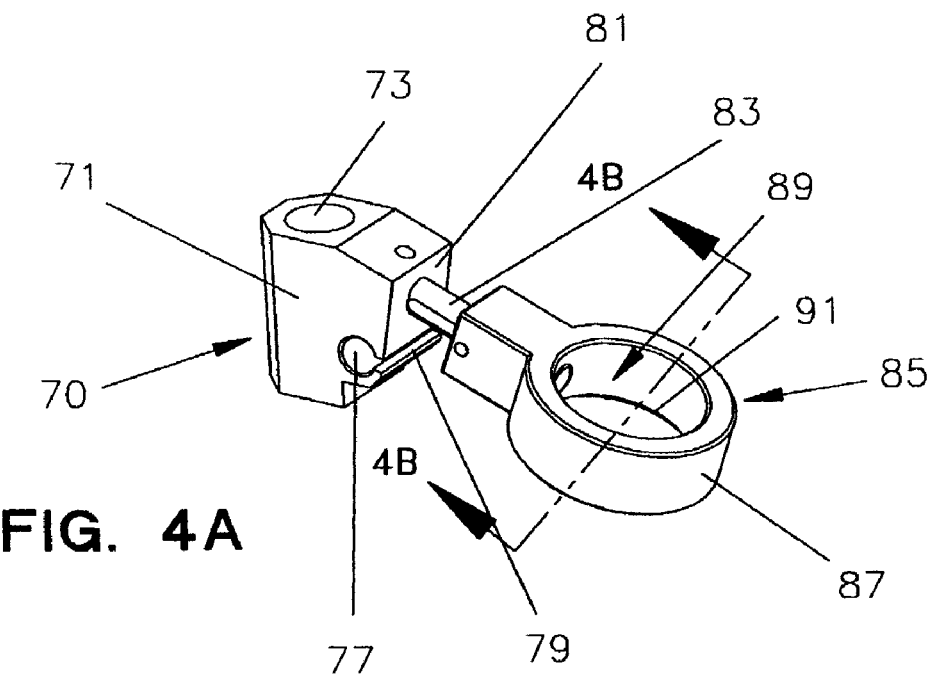
FIG. 4a shows a perspective view of the Femoral Neck Resector Guide sleeve and femoral head locator.
Figure 4B:
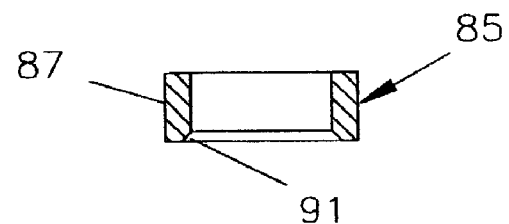

With reference, first, to FIGS. 1, 2, 3a and 3b, the heart of the instruments of the present invention consists of an intramedullary femoral broach (the broach) generally designated by the reference numeral 10. With particular reference to FIG. 2, the broach 10 has an elongated body including a proximal portion 11 and a distal portion 13. The proximal and distal portions are separated by an annular buttress 15 that includes a distally facing shoulder 19 and a proximally facing shoulder 22.

With further reference to FIG. 2, the proximal portion 11 of the broach 10 consists of a smooth cylindrical body having a proximal termination consisting of a coupling 21 for the handle 25 seen in FIG. 1.

With reference to FIG. 1, the handle 25 includes a gripping portion 27 of any desired shape, a stem 29, and a distal termination 31 consisting of a handle coupling having an inner chamber 33 (shown in phantom) that is sized and configured to couple with the proximal broach coupling 21 of the broach 10 to allow releasable attachment between the broach 10 and the handle 25. The interrelationship between the couplings 21 and 33 allows coupling of the handle 25 to the broach 10 in any one of a multiplicity of relative rotative orientations therebetween.

With reference back to FIG. 2, distal of the buttress 15, the distal portion 13 of the broach 10 is multi-sided having a multiplicity of cutting flanges that allow the tip 35 thereof to manually cut bone surface. With reference to FIGS. 3a and 3b, in the preferred embodiment, the distal portion 13 of the broach 10 has six sides defining sharp cutting edges 41, 43, 45, 47, 49 and 51 therebetween (FIG. 3B), and adjacent sides have, therebetween, respective longitudinally extending grooves or channels, each of which is designated by the reference numeral 53. The lateral terminations of each side are sharp edged cutting edges. The distal portion 13 of the broach 10 includes a sharp distal point 35 and conical surfaces 55 that subtend an angle, preferably 30 degrees, with respect to the longitudinal axis 59 of the broach 10 (FIG. 3a). As is seen in FIG. 3a, in particular, the grooves or channels 53 have distal terminations that are generally triangular and designated by the reference numeral 61, and which terminate slightly proximally of the pointed tip 35.

Figure 6:
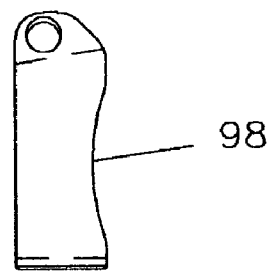
FIG. 6 shows a top view of the slotted cutting head.
Figure 7:
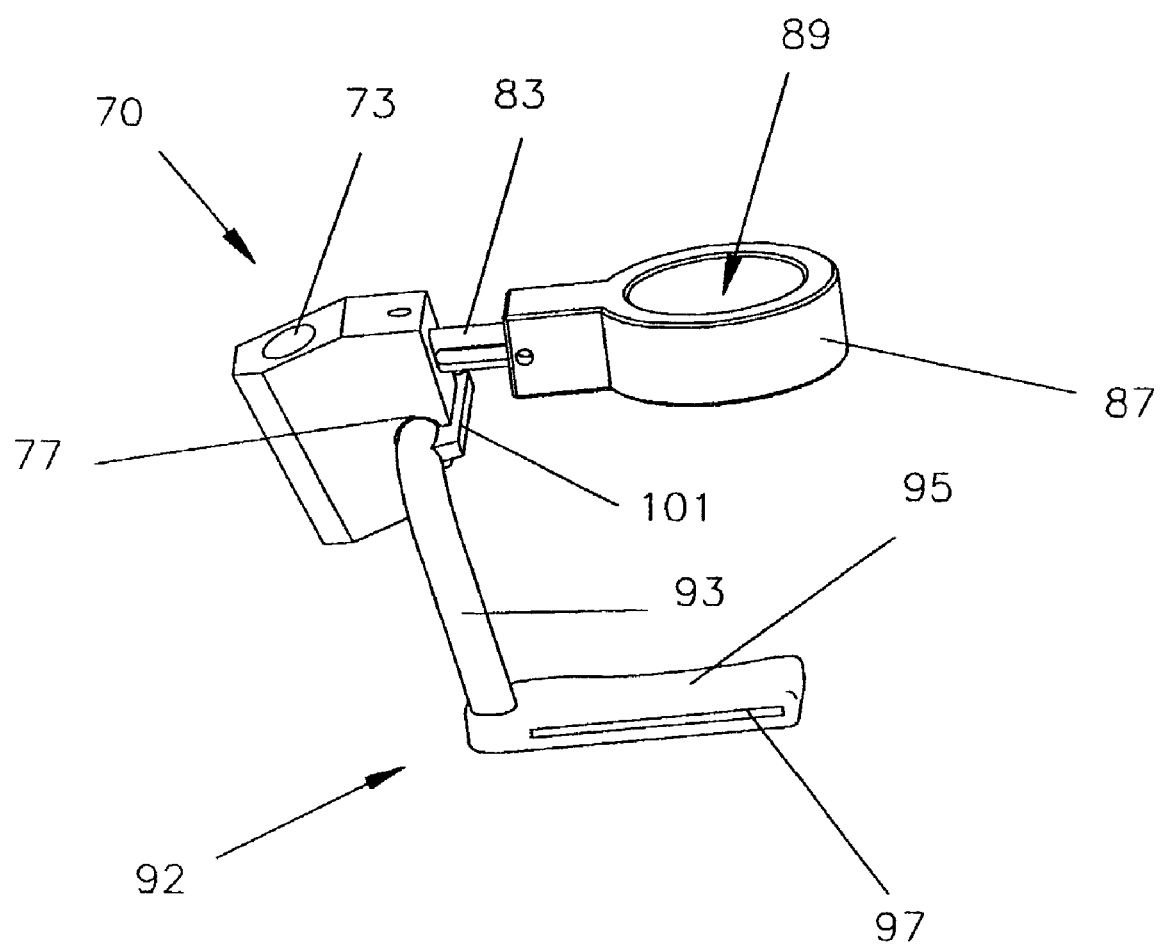
FIG. 7 shows a perspective view of the Femoral Neck Resector Guide sleeve and femoral head locator assembled with the cutting arm and slotted cutting head.
Figure 8:
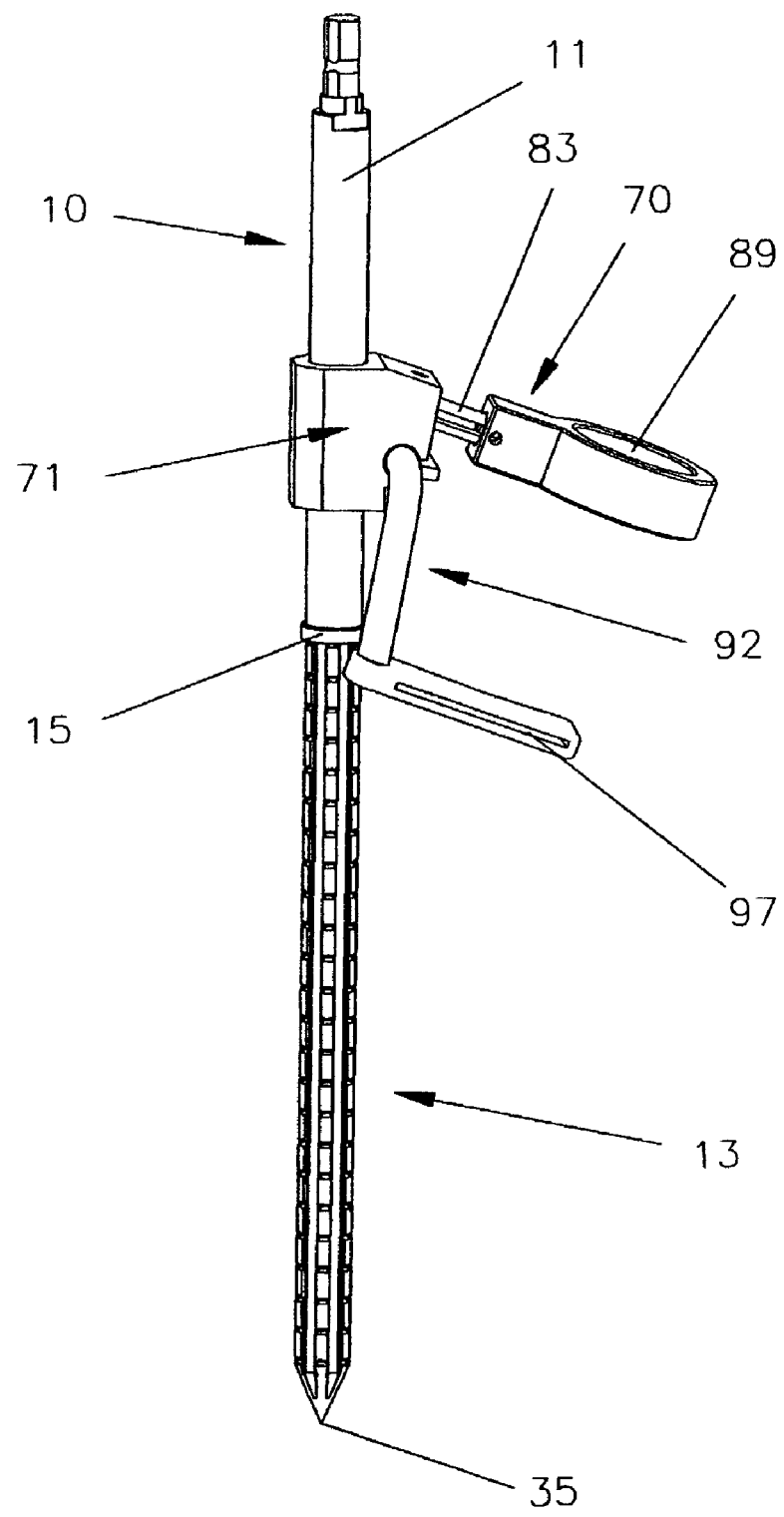
FIG. 8 shows a perspective view of the Femoral Neck Resector Guide assembled onto the Intramedullary Femoral Broach.

Now, with reference to FIGS. 4a-9, the femoral neck resector guide and cutting arm will now be described. With reference, first, to FIG. 4a, the femoral neck resector guide is generally designated by the reference numeral 70 and is seen to include a body 71 having an axial passageway 73 therethrough sized and configured to slide over the proximal portion 11 of the broach 10 (FIGS. 8 and 9).

With further reference to FIG. 4a, the guide 70 includes a generally cylindrical horizontal passageway 77 having a posteriorly facing elongated slot or keyway 79. The passageway 77 and slot 79 are provided for a purpose to be described in greater detail hereinafter. With further reference to FIG. 4a, extending laterally from a rear surface 81 of the body is a stem or extension rod 83 to which is attached an adjustable ring 85 having a periphery 87 and a central opening 89. The ring 85 opening 89 has a bottom peripheral chamfered edge 91 (FIG. 4b) that is designed to sit on top of the femoral head 3 (FIG. 9). When the chamfered ring 85 sits flush on top of the femoral head, this denotes the height and angle of anteversion (anterior rotation of the femoral head) from the axial center of the femoral shaft. The positioning of the ring 85 determines the height and angle of resection of the femoral head as well as the correct amount of anteversion of the resection with respect to the ring 85.

Figure 5:
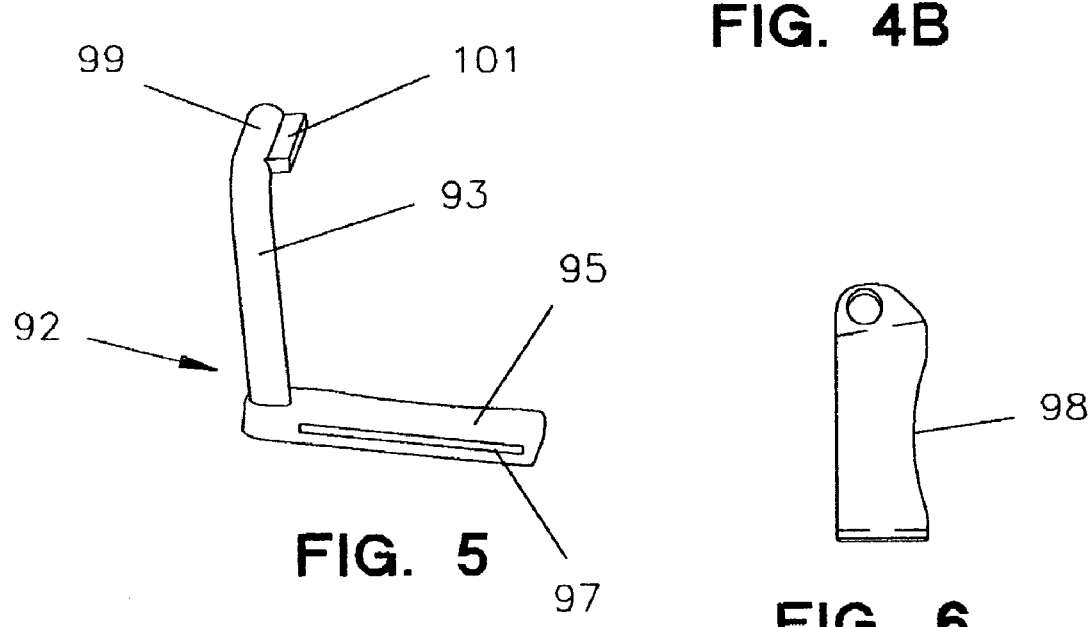
FIG. 5 shows a perspective view of the Femoral Neck Resector Guide cutting arm with the attached slotted cutting head.

With reference to FIG. 5, a cutting arm-cutting head 92 consists of a cutting arm 93 and a cutting head 95 having a slot 97 horizontally extending therethrough to guide the resection saw blade. With reference to FIG. 6, the cutting head has a contoured surface 98 adjacent to the femoral neck that is slide adjusted to fit all sized femoral necks. The cutting arm includes a horizontal cylindrical portion or rod 99 and a posteriorly facing protrusion or key 101. As should be understood with reference back to FIGS. 4a and 4b and with reference to FIGS. 7-9, the horizontal cylindrical portion or rod 99 is sized and configured to slide into the horizontal passageway 77 of the guide 70 with the protrusion 101 entering the horizontal slot 79 of the guide 70. The interconnection between the cutting arm-cutting head 92 and the guide 70 is seen in FIGS. 7-9. As should be understood, the cutting arm-cutting head can be made to enter the horizontal passageway 77 and slot or keyway 79 of the guide 70 from the opposite side as compared to that which is shown in FIGS. 7-9. In such case, the cutting arm-cutting head 92 is made in a mirror image of that which is shown, in particular, in FIGS. 5, 6, 7, 8 and 9. These mirror image cutting arm-cutting heads are intended to guide resection of left and right femurs, respectively.

Figure 9:
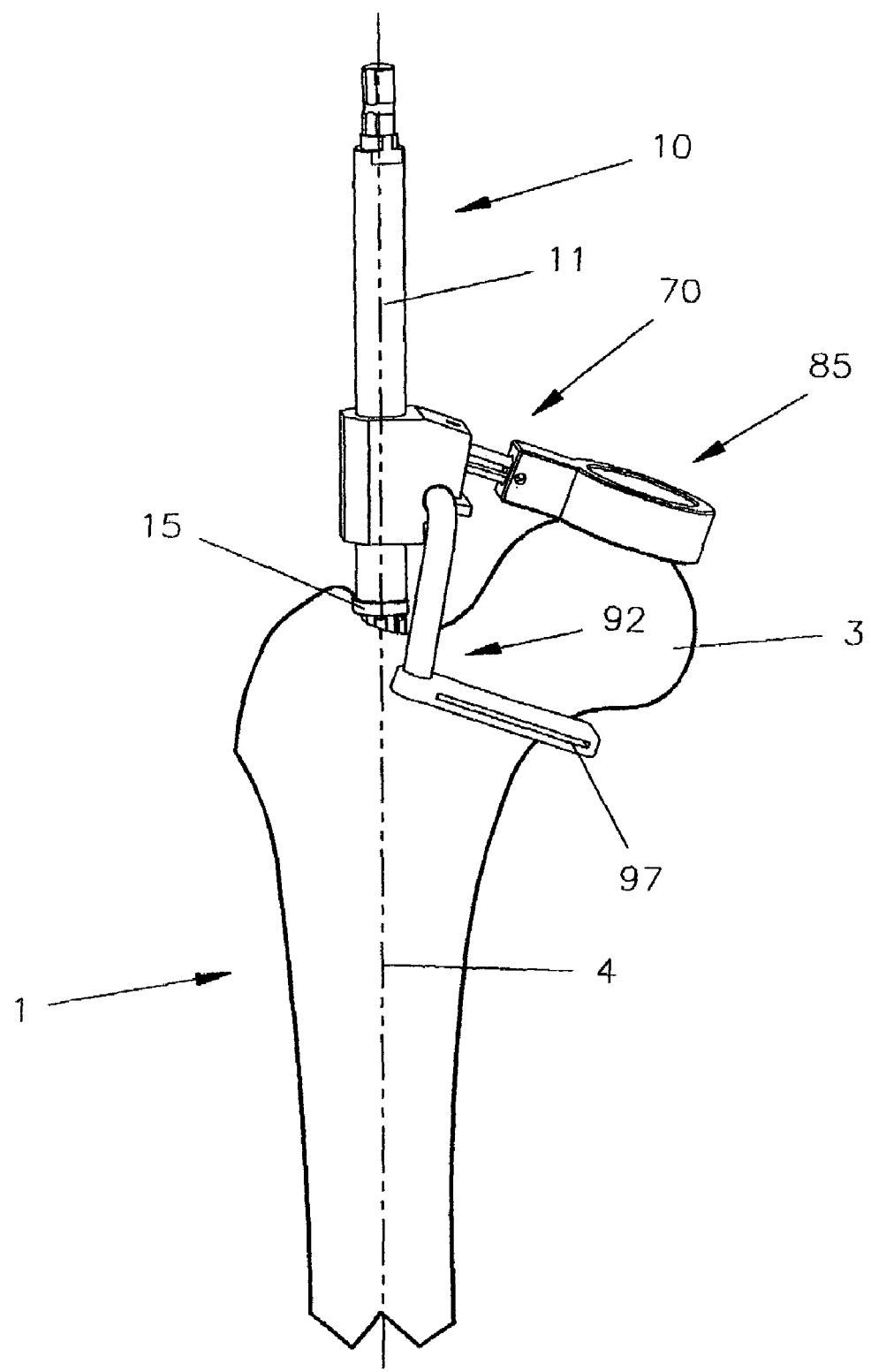
FIG. 9 shows a perspective view of the assembled Femoral Neck Resector Guide on the Intramedullary Femoral Broach within the proximal femur bone before the femoral neck resection.

FIG. 9 shows the assembly of the guide 70 and the cutting arm-cutting head 92 onto a femur 1 having a femoral head 3 and an axis of elongation 4. As shown in FIG. 9, the adjustable ring 85 sits on top of the femoral head 3 and the saw guide slot 97 is in precise position to properly resect the femoral head 3. The distal end of the broach 10 is not seen in FIG. 9 because it has been inserted within the intermedullary canal of the femur 1 in proper alignment to provide reference for location of the alignment of the cutting guide slot 97.

Figures 10, 11:
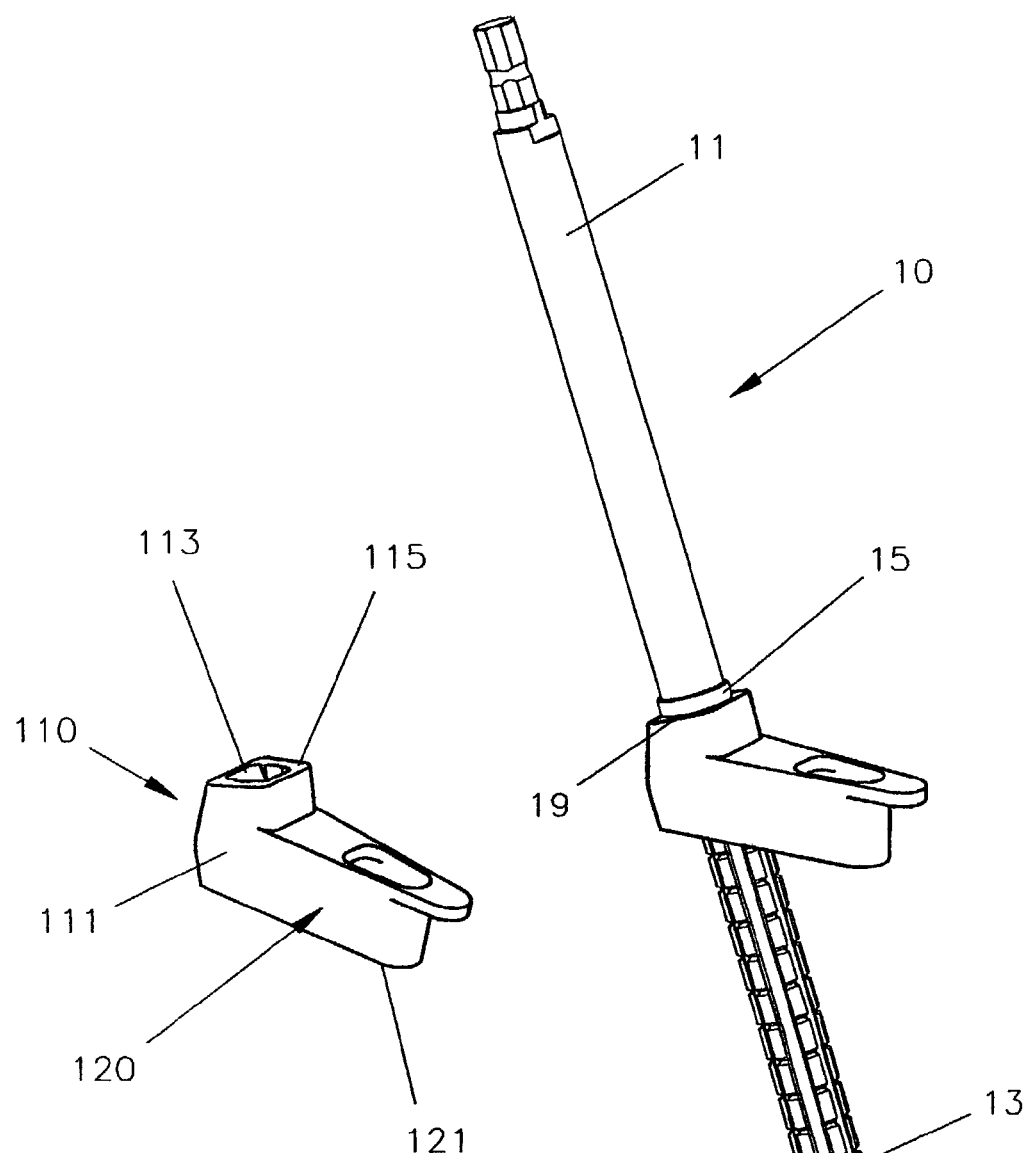
FIG. 10 shows a perspective view of the Sizer/Cutter Template.
FIG. 11 shows a perspective view of the Sizer/Cutter Template assembled onto the Intramedullary Femoral Broach.

FIG. 10 shows a sizer/cutter template 110 that includes a body 111 with an opening or passageway 113 therethrough sized to slide upwardly from the tip 35 of the broach 10 to the downwardly facing shoulder 19 of the buttress 15 (FIG. 1). The body 111 has a top or upper surface 115 that is designed to engage the shoulder 19 of the buttress 15 of the broach 10 (FIG. 11) for a purpose to be described in greater detail hereinafter. Extending obliquely from the body 111 is a template 120 that includes an undersurface defined by a peripheral cutting edge 121 that resembles a "cookie cutter" and clearly demarks bone that is to be removed in a manner known to those skilled in the art to thereby facilitate a precise fit of a femoral head prosthesis. The template 120 can easily be adjusted to the precise angulation of the femoral anteversion of the particular patient. FIG. 11 shows the assembly of the template 110 on the femoral broach 10. The template is easily pounded into the bone of the femur 1 due to the interaction between the buttress 15 shoulder 19, and the top surface 115 of the body 111 of the sizer/cutter template 110. To drive the sizer/cutter template 110 into the proximal femur, with the handle 25 installed on the broach 10 (FIGS. 1 and 2), the top of the handle 25 is struck repeatedly until the template 120 is appropriately driven into the proximal femur.

Figure 12:
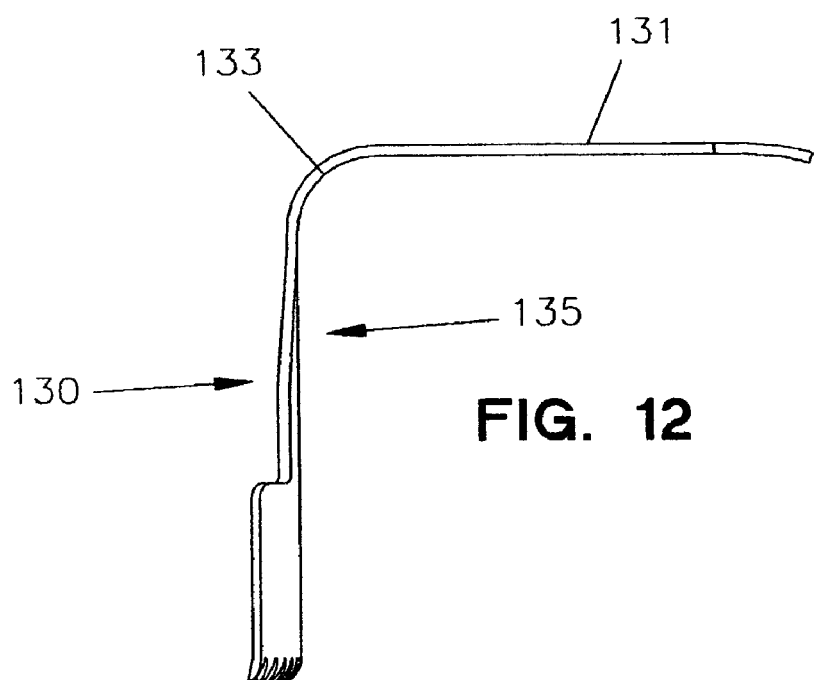
FIG. 12 shows a side view of the Anterior Acetabulum Retractor.
Figure 13:
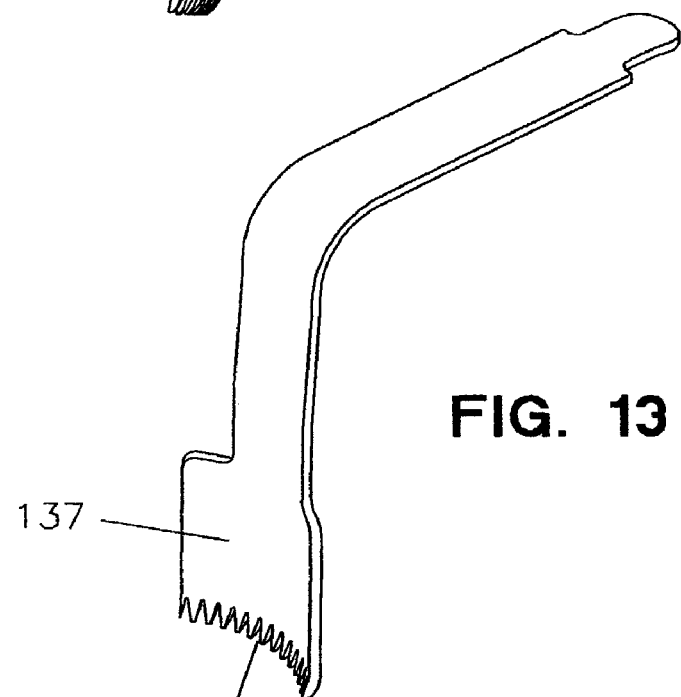
FIG. 13 shows a perspective view of the Anterior Acetabulum Retractor.
Figure 14:
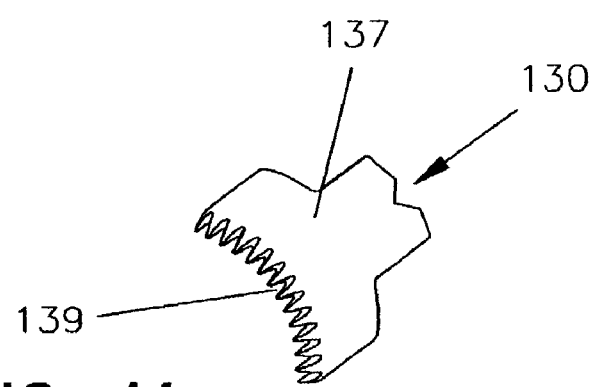
FIG. 14 shows a perspective view of the Anterior Acetabulum Retractor proximal curved tip with angulated fixation teeth.

With reference, now, to FIGS. 12-14, the anterior acetabulum retractor is generally designated by the reference numeral 130 and includes an L-shaped configuration including a distal handle portion 131, a substantially right angle bend 133, and a proximal portion 135 having a proximal termination or end 137 that is arcuate and has a plurality of proximal angulated teeth 139 formed on an arcuate surface thereof. The retractor 130 is essentially a right angled retractor curved backwards to allow the surgeon to push it upwardly to retract the overlying tissues. The curved portion with angulated teeth 139 is designed to fit onto the superior acetabulum and acts as a fulcrum for elevating the tissues away from the acetabulum. In the preferred mode of surgery, the desired angle of retraction is roughly 45 degrees to minimize tissue disruption so that the proximal arm is relatively long compared to standard retractors.

With the instruments of the present invention having been described, the preferred method of use of the instruments in performing total hip surgery will now be set forth.

Preferred Method of Use:

The Posterior Incision

1) Place the patient in the Lateral decubitus position on the operative table with anterior and posterior buttresses to stabilize the pelvis.
2) With the patients hip flexed 45 degrees and internally rotated. The entire table is rotated 15 degrees towards the patient=s belly button giving excellent visibility to the posterior aspect of the hip.
3) Just posterior to the greater trochanter, a 3-inch incision is made starting 2 inches above the tip of greater trochanter extending down 1 inch below the tip of the greater trochanter. The fascia latae is incised in the same plane. This exposes the external rotator muscle insertions along the intertrochanteric crest. The piriformis insertion is released first and tagged to be reattached to the posterior edge of the gluteus medius later. The remaining 4 external rotators with the underlying capsule is released from bone and incised longitudinally at its midpoint exposing the femoral head.
4) The hip is flexed and externally rotated dislocating the femoral head and neck posteriorly. Pushing the knee proximally exposes more femoral head and neck. Use a POSTERIOR FEMORAL NECK RETRACTOR to hold the femoral head and neck out of the wound.
5) The piriformis fossa is located on the undersurface of the greater trochanter posteriorly. A sharp STARTING PUNCH is used to create a starting hole for the IM broach 10 just anterior to the pirformis fossa. Keep the hole as lateral as possible. Insert the INTRAMEDULLAY BROACH 10 (1) tip 35 into this hole and manually extend into the intramedullary canal. Always keep the broach 10 as lateral and straight as possible. Remove the T handle 25 from the broach.
6) Apply the FEMORAL NECK RESECTION GUIDE 70 (2) onto the IM broach rod while centering the circular ring 85 on the femoral head 3. Next, slide in the left or right CUTTING HEAD 92 into the posterior slot 77, 79 in the Resector Guide. Be sure to remove any impinging osteophytes over the posterior greater trochanter that impedes the cutting head from sitting flush on the posterior femoral neck. This will make the appropriate cut for a "medium neck" prosthesis for this particular prosthesis. It will also be appropriate for this patient's femoral anteversion.
7) The axis of rotation (anteversion) is easily determined by drawing a line from the center of the IM rod 10 to the most prominent portion on the neck (calcar). Measure this distance with a ruler. In this system the femoral neck determines the largest possible prosthesis that can be used in this patient. Chose the closest SIZER/CUTTER TEMPLATE 110 (3) under your measured number.
8) Now remove the IM Broach rod 10 and apply the sizer/cutter 110 onto the rod from the bottom up until it stops on a buttress 15. Reapply the T-handle 25 and adjust the sizer/cutter 110 in line with your previous determined axis of rotation (anteversion). Use a mallet to pound the SIZER/CUTTER 110 into the proximal femoral neck and greater trochanter. The axial IM rod 10 makes sure the template does not slide into varus (downward tilt).
9) Since this is proximal press fit prosthesis with decreasing tapers in three planes the isthmus, (smallest cross-section of the femoral canal) is not a big concern. Use a COMPRESSING BROACH slightly under sized from the TEMPLATE SIZE to compress the remaining cancellous bone. You have now finished the preparation of the femoral canal.

The Anterior Incision

1) Tilt the operative table 15 degrees posterior for better visibility of the anterior hip area.
2) Make a 3-inch incision starting 2 inches medial and one inch distal to the tip of the greater trochanter. Develop the interval between the Sartorius and the Tensor fascia latae muscles. Extend your finger onto the femoral neck and identify the insertion of the femoral capsule along the anterior inter-trocanteric line. Sharply excise the capsule from bone. This will be easier because the remaining femoral neck will be dislocated posteriorly.
3) Make a longitudinal incision in the capsule and free up the capsule from the superior acetabulum so the ANTERIOR ACETABULUM RETRACTOR 130 (4) can be locked onto the edge of the superior acetabulum. Use two cobra retractors one anterior and one posterior to expose the entire acetabulum. This will give the surgeon a straight shot for reaming the acetabulum at 40 degrees abduction and 20 degrees adduction (anteversion of the cup).
4) Bone graft any residual bone cysts and press fit the trial cup into the acetabulum. Apply the femoral trial through the posterior incision and reduce the components. Holding the leg in slight flexion in neutral alignment, the components should be concentric. Test for stability both posteriorly and anteriorly. The most important part of the operation is component position and stability take your time to be sure it is correct. When satisfied with the concentricity of the components press fit the final components into place. Be sure to reattach the external rotators with the underlying capsule back to the inter-trochanteric crest through a couple drill holes in bone. This is the preferred method of use of the four denoted (1-4) instruments.

The invention claimed is:

1. In an instrument system for preparing a proximal femur for total hip replacement, the improvement comprising an intermedullary femoral broach, including:
   a) an elongated body having a proximal portion, a distal portion, and a buttress between said portions;
   b) said proximal portion having smooth outer walls and a proximal end, said smooth outer walls having a substantially constant cross-sectional configuration proximal of said buttress such that an instrument may be slid along said proximal portion from said proximal end toward said buttress;
   c) said distal portion having a sharp pointed distal end and peripheral walls including a plurality of linear longitudinally extending parallel cutting edges; and
   d) a femoral neck resector guide, comprising:
      i) a body having an opening therethrough permitting said body to slide over said outer walls of said proximal portion of said broach; and
      ii) a ring extending laterally of said body;
      iii) said ring sized to sit on top of a femoral head of a femur when said distal portion of said broach is placed within an intermedullary canal of said femur.

2. The system of claim 1, wherein said buttress comprises an annular protrusion including a proximally facing shoulder and a distally facing shoulder.

3. The system of claim 1, wherein said proximal end of said proximal portion includes a broach coupling.

4. The system of claim 3, further including a handle having a handle coupling releasably attachable to said broach coupling.

5. The system of claim 1, wherein said distal portion has an outer surface comprising a plurality of flat surfaces, adjacent ones of said flat surfaces meeting at longitudinally extending sharp edges comprising said cutting edges.

6. The system of claim 5, wherein each of said flat surfaces includes two coplanar portions separated by a longitudinally extending groove.

7. The system of claim 5, wherein said plurality of flat surfaces comprises six surfaces.

8. The system of claim 7, wherein each of said flat surfaces includes two coplanar portions separated by a longitudinally extending groove.

9. The system of claim 8, wherein six longitudinally extending grooves are provided.

10. The system of claim 1, wherein said ring is connected to said body with an extension rod permitting said ring to self center on said femoral head.

11. The system of claim 1, wherein said ring is located to determine height and angular rotation (anteversion) of resection of a femoral neck.

12. The system of claim 1, further including a horizontal passageway through said body, and a cutting head having a body with a saw blade guiding slot therethrough and a rod receivable within said horizontal passageway to releasably attach said cutting head to said guide body.

13. The system of claim 12, wherein said cutting head has a lateral surface contoured to fit snugly against a patient's bone.

14. The system of claim 12, wherein said cutting head comprises a left cutting head adapted to guide resection of a left femoral head, said system further including a right cutting head symmetrical to said left cutting head and adapted to be receivable in said horizontal passageway from an end opposite to an end by which said left cutting head rod is insertable into said horizontal passageway, said right cutting head being adapted to guide resection of a right femoral head.

15. The system of claim 12, wherein said horizontal passageway has a locking keyway adjacent thereto and said rod has a key extending therefrom and entering said locking slot when said rod enters said horizontal passageway to fix a rotative orientation of said cutting head with respect to said guide.

16. The system of claim 1, further including a template having a body with an opening therethrough sized to be slidably received over said distal portion of said broach, and an undersurface having a sharp periphery adapted to cut into a proximal femur after a femoral head thereof has been resected.

17. The system of claim 16, wherein said buttress comprises an annular protrusion including a proximally facing shoulder and a distally facing shoulder.

18. The system of claim 17, wherein said template body has an upper surface adapted to engage said distally facing shoulder of said buttress.

19. The system of claim 18, wherein said proximal end of said proximal portion includes a broach coupling, further including a handle having a handle coupling releasably attachable to said broach coupling.

20. The system of claim 19, wherein said handle is T-shaped and has a proximal surface adapted to be struck to drive said undersurface of said template into said proximal femur.

21. The system of claim 16, wherein said peripheral walls of said distal portion of said broach and said template body opening have complementary non-circular cross-sections, thereby locking a rotative orientation of said template on said broach.

22. In an instrument system for preparing a proximal femur for total hip replacement, the improvement comprising an intermedullary femoral broach, including:
   a) an elongated body having a proximal portion, a distal portion, and a buttress between said portions;
   b) said proximal portion having smooth outer walls and a proximal end;
   c) said distal portion having a sharp pointed distal end and peripheral walls including longitudinally extending cutting edges; and
   d) a femoral neck resector guide, comprising:
      i) a body having an opening therethrough permitting said body to slide over said outer walls of said proximal portion of said broach; and
      ii) a ring extending laterally of said body;
      iii) said ring sized to sit on top of a femoral head of a femur when said distal portion of said broach is placed within an intermedullary canal of said femur; and
      iv) said ring being connected to said body with an extension rod permitting said ring to self center on said femoral head.

* * * * *